US00PP09089P

United States Patent [19]

Yamagishi et al.

[11] Patent Number: Plant 9,089

[45] Date of Patent: Mar. 21, 1995

[54] MANILA GRASS VARIETY GS90-18

[75] Inventors: Takashi Yamagishi, Hokkaido; Kenichi Nakagawa, Tokyo; Kouichi Mitsui, Katori; Shigeki Nagatomi; Kenzo Miyahara, both of Mito, all of Japan

[73] Assignee: Sumitomo Metal Industries, Ltd., Osaka, Japan

[21] Appl. No.: 40,293

[22] Filed: Mar. 30, 1993

[51] Int. Cl.[6] ..... A01H 5/00

[52] U.S. Cl. ..... Plt./90

[58] Field of Search ..... Plt. 90

*Primary Examiner*—James R. Feyrer

*Attorney, Agent, or Firm*—James C. Weseman

[57] ABSTRACT

Manila grass (also South Japanese grass; *Zoysia matrella* L.) usually completely withers at the leaf part in winter in an area where frost occurs. The present variety of Manila grass is characterized by the ability to maintain green leaves (evergreen) in a whole year, a trait which has not been observed in other Manila grass varieties.

The general characteristics of the present variety include somewhat straight grasses, slender leaf blades, and vividly green leaves, as well as dense greens which can be maintained in all seasons. The variety is somewhat resistant to turfgrass rust disease and is also resistant to usual pests, thereby reducing the cost of pesticides. In addition, the frequency of sprinkling, fertilization, and trimming can be reduced, so that labor can be saved in cultivating the variety.

7 Drawing Sheets

TECHNICAL FIELD

The present invention comprises a new and distinct variety of Manila Grass, botanically knwon as *Zoysia matrella* L., and hereafter referred to by the variety name GS90-18.

SUMMARY OF THE NEW VARIETY

The present variety, GS90-18 is an evergreen variety selected from clonal progeny mutated by acute acute irradiation of a stolon mat of Tsukuba line (*Zoysia matrella* L. Manila grass culture line) with gamma rays (source: Co). The variety was then vegetatively propagated by stolons.

Evergree variety GS90-18 possesses the characters of keeping stems and leaves green for the entire year and not becoming dormant in areas where stems and leaves usually wither and become dormant owing to low temperature in winter.

Variety GS90-18 was evaluated for an evergreen trait and for adaptation to entironmental circumstances as general characteristics. It was found that the present variety, while retaining the same general characteristics as those of the original variety (Tsukuba line), was induced by mutation with a unique evergreen trait not previously observed in Zoysia grasses.

This plant is less prone to go dormant with lower seasonal temperatures and requires less mowing, it may be more attractive for use as a residential turf grass as compared to other available Manila gress varieties. The stolons of the present variety are of strong elongation and can form a dense mat.

The plant of this invention may be advantageously used because it forms a sod so dense that weed infestation is reduced. The present variety GS90-18 has treading resistance, drought resistance, salt resistance and shade tolerance. Since vegetatively propagated turf is vulnerable to invasion by weeds, weeds can be eliminated by application of herbicides. Alternatively, turfgrass can be grown rapidly after planting, so as to form complete turf.

Stolons of the present variety can rapidly form a mat. Furthermore, variety GS90-18 provides a green carpet in all seasons for use planting in a city park. In a residential application, it is possible to conserve labor and greatly reduce the time which previously has been required for trimming, etc. with known varieties of Manila grass.

Asexual Reproduction

The predecessor variety, "Tsukuba" line, is not sterile although both the number of seeds and the percentage of seed germination are not high, and this variety is practically propagated not via propagation from seeds, but exclusively via vegetative propagation.

The original variety, Tsukuba line, forms complete turf in 1 year by vegetative propagation from stolon mats (each about 10×10 cm) implanted at intervals of about 15×15 cm.

The present variety, GS90-18, has been asexually reproduced by stolon cultures in the facilities of the owner of the variety in Japan. All propagules observed to date have been true to the original variety. This asexual reproduction was conducted in Hasaki Research Center, Sumitomo Metal Industries, Ltd. (Lat 35°44′ N and Long. 140°50′ E in Hasaki Town, Ibaragi Prefecture, Japan).

DESCRIPTION OF THE NEW VARIETY

Figure 1:
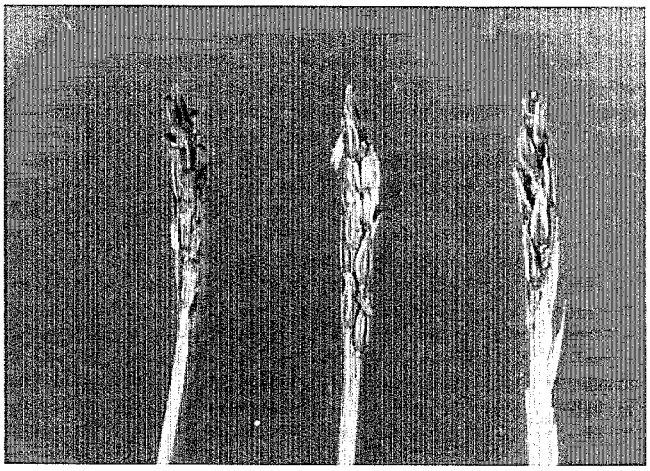
FIG. 1 is a photograph of spikes collected in the same place, and shows the variety Meyer (right), Tsukuba line (middle) and the present vareity GS90-18 (left), respectively. Meyer spikes are deep reddish purple (expressed according to Japan Garden ISCC-NBS), Code No. 9210 (expressed according to Japan Garden Plant Standard Color Sheets compiled by the Ministry of Agriculture, Forestry and Fisheries (1977)) (hereinafter, this standard is used for color expression), and both GS90-18 and Tsukuba line spikes are deep reddish purple (Code No. 8916). Their pollen indicates the characteristic of fertility.
Figure 2:
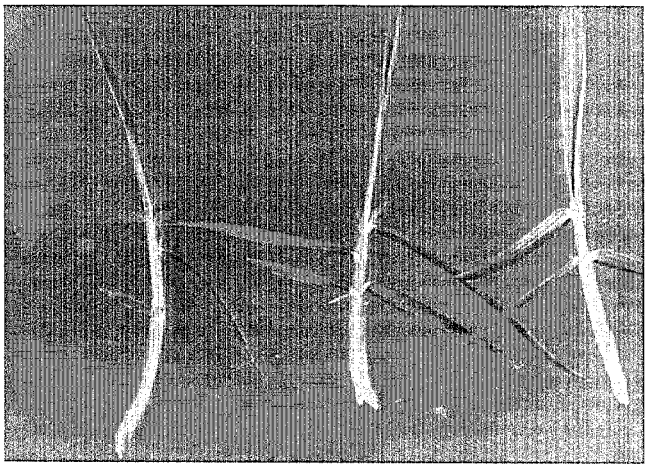
FIG. 2 is a photograph of connecting parts of leaf and leaf sheath, and shows Meyer (right), Tsukuba line (middle), and the present variety GS90-18 (left), respectively. In Meyer, no auricle is present and the ligule is small; 1 mm or less hairs radially extend from the ligule and 1–3 mm hairs radically extend from the top of the leaf sheath. The Tsukuba line and GS90-18 are morphologically similar where no auricle is present and the ligule is small; 1–2 mm hairs radically extend from the ligule; and 1–3 mm hairs are present on the terminal of the leaf sheath on the auricle side.
Figure 3:
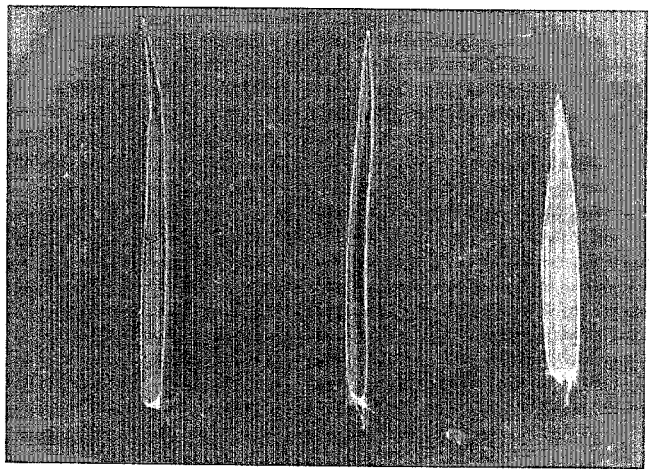
FIG. 3 is a photograph of matured primary leaves showing Meyer (right), Tsukuba line (middle) and the present variety (GS90-18 (left). The Meyer leaf is 3.9 cm long and 3.6 mm wide, which is broad, flat and hair-free, and the color is dark olive green (Code No. 3707) and the back of the leaf is lustrous. The Tsukuba line leaf is 7.7 cm long and 1.7 mm wide and the GS90-18 leaf is 7.1 cm long and 1.9 mm wide, both of which are slightly concave leaves, hair-free and deep yellow green (Code No. 3706) and the back of the leaves is lustrous.
Figure 4:
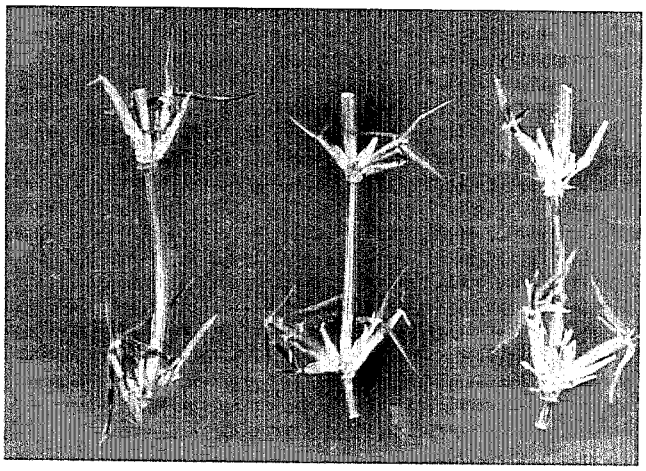
FIG. 4 is a photograph of the nodes of matured runners grown under the same cultural conditions. The exposed stems of GS9018 (left) and Tsukuba line (middle) both are dark reddish purple (Code No. 9218), and the stems inside the leaf sheaths are moderate yellow green (Code No. 3312). In this respect, there is no particular difference from Meyer.
Figure 5:
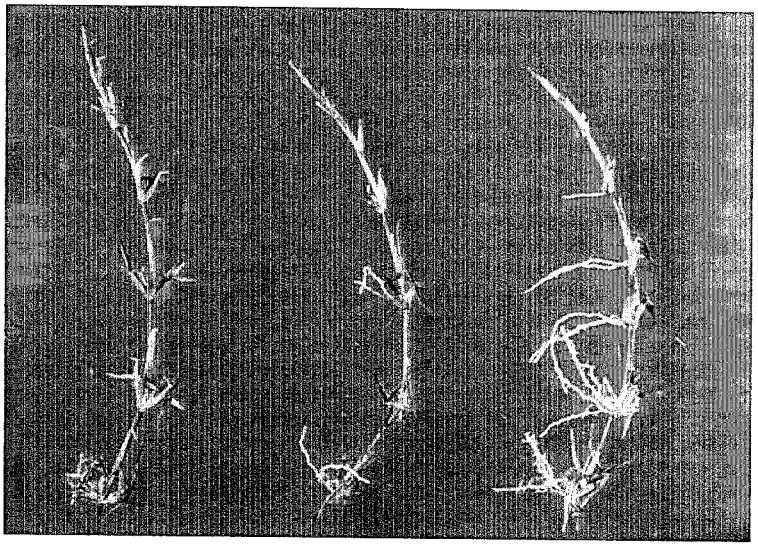
FIG. 5 shows a shape of runners collected from the same place. As compared with Meyer (right), GS9018 (left) and Tsukuba line (middle) have slightly slender stems and the same degree of length of internode.
Figure 6:
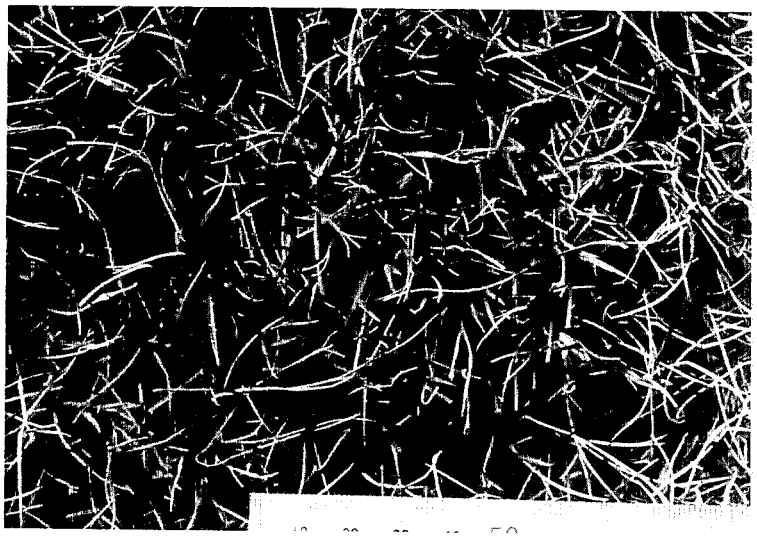
FIG. 6 is a photograph of the variety of the present application, GS90-18.
Figure 7:
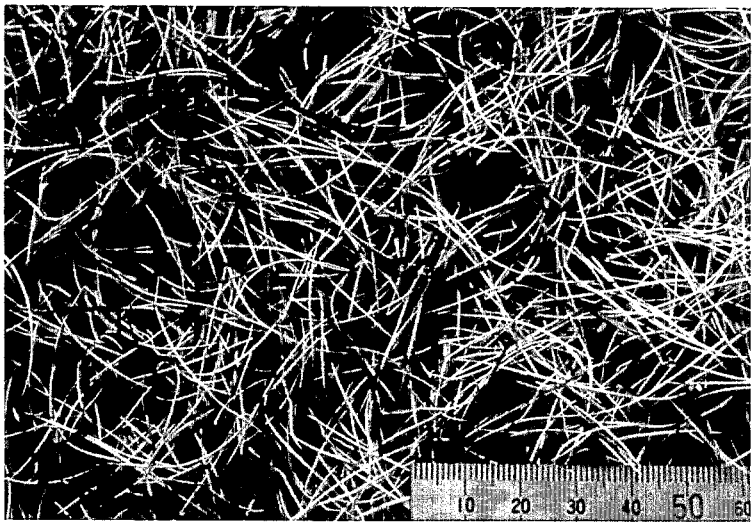
FIG. 7 is a photograph of the predecessor variety, Tsukuba line (the Korean lawn grass)
Figure 8:
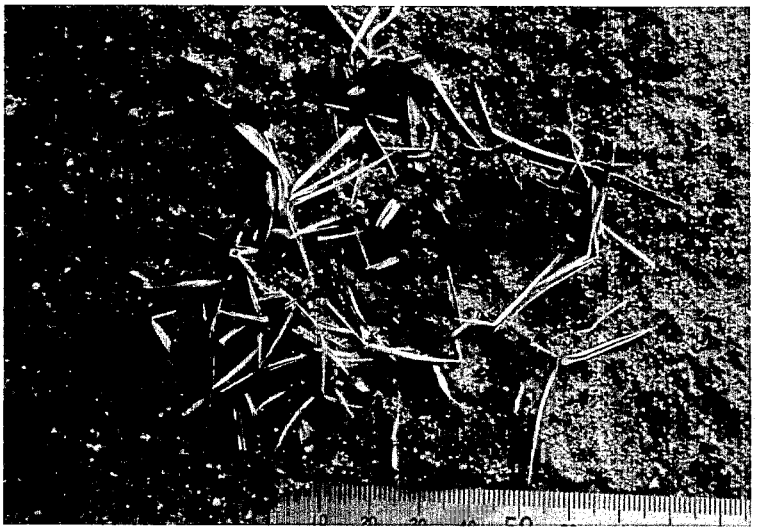
FIG. 8 is a photograph of the standard variety Meyer.
Figure 9:
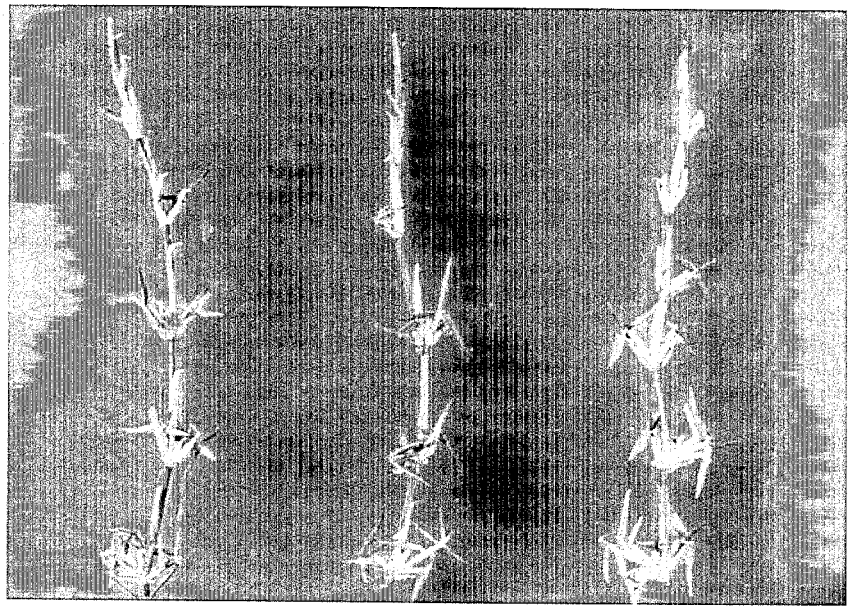
FIG. 9 shows shape of runners collected from the same place. The roots have been removed from the Meyer (right), GS90-18 (left) and Tsukuba lines.

The Tsukuba line is a culture line from *Zoysia matrella* L., and is widely used as turf in the home and as a green in a golf course in the Kanto area in Japan. The morphological characteristics of the Tsukuba line and the variety Meyer are as follows: leaf angle of 25° (Tsukuba line) and 20° (Meyer); leaf length of 7.7 cm (Tsukuba line) and 3.9 cm (Meyer); leaf width of 1.7 mm (Tsukuba line) and 3.6 mm (Meyer); stolon thickness 0.95 mm (Tsukuba line) and 1.47 mm (Meyer); thickness of spikestem of 0.5 mm (Tsukuba line) and 0.7 mm (Meyer); length of spikestem of 5.6 cm (Tsukuba line) and 5.0 cm (Meyer); length of spike of 15.2 mm (Tsukuba line) and 22.7 mm (Meyer); length of spikelet 2.6 mm (Tsukuba line) and 2.7 mm (Meyer); width of spikelet of 20 per spike (Tsukuba line) and 33 (Meyer); and weight of 291 mg per 1000 seeds (Tsukuba line) and 325 mg (Meyer). Like other Zoysia grasses. The Tsukuba line is dormant in winter, and the dormant period of Tsukuba line is about 3 months from early December to early March of the next year, while that of Meyer is about 4 months from early November to early April of the next year (Lat. 35°44′ N and Long. 140°50′ E in Hasaki Town, Ibaragi Prefecture, Japan).

Manila grass variety GS90-18 displays an evergreen characteristic in winter while retaining the desirable commercial characteristics of the predecessor variety, Tsukuba line.

The Tsukuba line and the comparative variety Meyer enter a withered state in winter for 3 to 4 months in warm areas in Japan, but the present variety GS90-18 is not dormant in winter. Occasionally, coloration occurs in the variety to some extend due to anthocyanin in the back of the leaf blades or in the stolons at the beginning of winter. The leaf blandes of the present variety display strong resistance to dormancy in winter, and this evergreen characteristic has not been seen in other Zoysia grasses.

GS90-18 was created from the original variety Tsukuba line, as follows: Stolon mats of Tsukuba line were irradiated with gamma rays in July 1990 in Institute of Radiation Breedings of National Institute of Agrobiological Resources, the Ministry of Agriculture, Forestry and Fisheries (Lat. 36°31′ N and Long. 140°23′ E in Ohmiya Town, Ibaragi Prefecture, Japan) and an optimal irradiation was determined. That is, 129 stolon mats 30 cm long and 15 cm wide were irradiated with gamma rays at 50-250 Gy for 72 hours ($^{60}$Co source, 44.4 TBq). After irradiation, each mat was divided into stolon stems each with 2–3 nodes and then implanted in Hasaki Research Center. (Sumitomo Metal Industries, Ltd. (Lat. 35°44′ N and Long. 140°50′ E in Hasaki Town, Ibaragi Prefecture). Thereafter, they were primarily screened for green sports so that 67 mutants in total were selected in winter by February of 1991, 3 years thereafter, the resultant evergreen mutants were evaluated for their characteristics, and as a result, the present variety GS9018 was obtained from one sport which was induced with 50 Gy gamma rays. Therefore the propagules or GS 90-18 consits of one genotype.

For comparison, the morphological characteristics etc. of the thus obtained GS90-18, together with those of the control variety Meyer and the original variety Tsukuba line, are set forth below:

TABLE 1

COMPARISON OF SPROUTING TIME AND COLORING TIME

| Variety | sprouting time (spring) | coloring time (autumn) |
|---|---|---|
| GS90-18 | the end of February | no coloring |
| Tsukuba line | the beginning of March | the beginning of December |
| Meyer | the beginning of April | the end of November |

Distinctive morphological characteristics of variety GS90-18 include slightly straight grasses of medium grass color, slightly long and narrow leaf blades, and slightly dense stolons of medium thickness.

TABLE 2

COMPARISONS OF LEAF ANGLE, LENGTH AND WIDTH

| Variety | leaf angle* | leaf length (cm) | leaf width (mm) |
|---|---|---|---|
| GS90-18 | 25° | 7.1 | 1.9 |
| Tsukuba line | 25° | 7.7 | 1.7 |
| Meyer | 20° | 3.9 | 3.6 |

*Angle between leaf and horizonal plane

TABLE 3

COMPARISON OF LEAF COLOR, NUMBER OF BRANCHES AND STOLON THICKNESS

| variety | leaf color* | No. of Branches per $m^2$ | stolon thickness (mm) |
|---|---|---|---|
| GS90-18 | deep yellow green | 38650 | 1.02 |
| Tsukuba line | deep yellow green | 35725 | 0.95 |
| Meyer | dark olive green | 30275 | 1.47 |

*descriptions according to ISCC-NBS

TABLE 4

COMPARISONS OF SPIKE STEM THICKNESS & LENGTH

| Variety | Thickness of spike stem (mm) | Length of spike stem (cm) |
|---|---|---|
| GS90-18 | 0.7 | 5.2 |
| Tsukuba line | 0.5 | 5.6 |
| Meyer | 0.7 | 5.0 |

TABLE 5

COMPARISONS OF SPIKE LENGTH AND COLOR

| Variety | Length of Spike (mm) | Color of Spike* |
|---|---|---|
| GS90-18 | 14.8 | deep reddish purple |
| Tsukuba line | 15.2 | deep reddish purple |
| Meyer | 22.7 | deep reddish purple |

*descriptions according to ISCC-NBS

TABLE 6

COMPARISONS OF SPIKELET LENGTH AND WIDTH

| Variety | Length of a Spikelet (mm) | Width of a Spikelet (mm) |
|---|---|---|
| GS90-18 | 2.3 | 0.7 |
| Tsukuba line | 2.6 | 0.7 |
| Meyer | 2.7 | 0.8 |

Upon sprigging GS9018 stolons aggressively grow to produce a dense, tough, durable, yet attractive turf of healthy appearance. The predecessor vareity, the present variety GS90-18, and Meyer exhibit similar elongation and rooting of runners. Once the turf has been established, the grass continues to grow activity in both spring and fall, and remains green all through the year under the conditions of the location of culture named above. Sod of this variety presents a healthy, recovered appearance immediately after mowing.

Although the present vareity GS9018 is basically vegetatively propagated, like other Zoysia grasses, it spouts spikes and produce a small amount of seeds.

The percentage of seed germination examined for the predecessor variety, the present variety GS90-18, and Meyer are of low and similar degree.

TABLE 7

COMPARISONS OF SPIKELETS PER SPIKE AND SEED WEIGHT AND SEED GERMINATION

| Variety | Number of Spikelets Per Spike | Weight of 1000 seed (Mg) | Seed Germination (%) |
|---|---|---|---|
| GS90-18 | 18 | 275 | 21 |
| Tsukuba line | 20 | 291 | 22 |
| Meyer | 33 | 325 | 20 |

Approximately 20 seeds per spike are usually produced.

The seeds are somewhat light, weighing approximately 250–300 mg per 1000 seeds.

Other than turfgrass rust disease, no particular pests were found to occur in variety GS90-18 during evaluation of the growth and characteristics thereof.

The resistance of the present variety to turfgrass rust disease was moderately high; equal to that of the Tsukuba line and higher than that of Meyer (low).

Figure 10A:
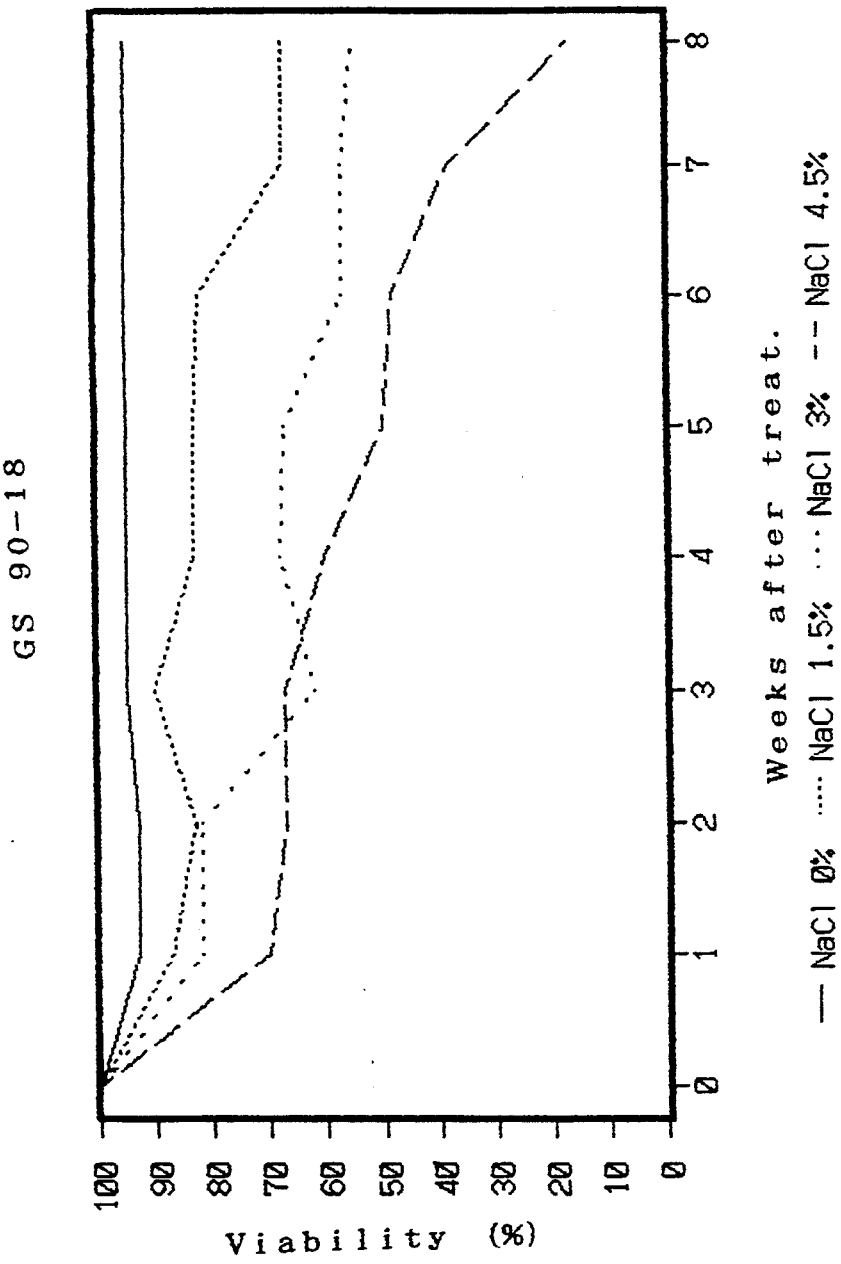
FIG. 10(*a*) and (*b*) shows salt resistance expressed as viability of GS90-18 compared to the Meyer line of plants exposed to either a 1.5%, 3.0% or 4.5% solution of NaCl for up to eight weeks after treatment.
Figure 10:
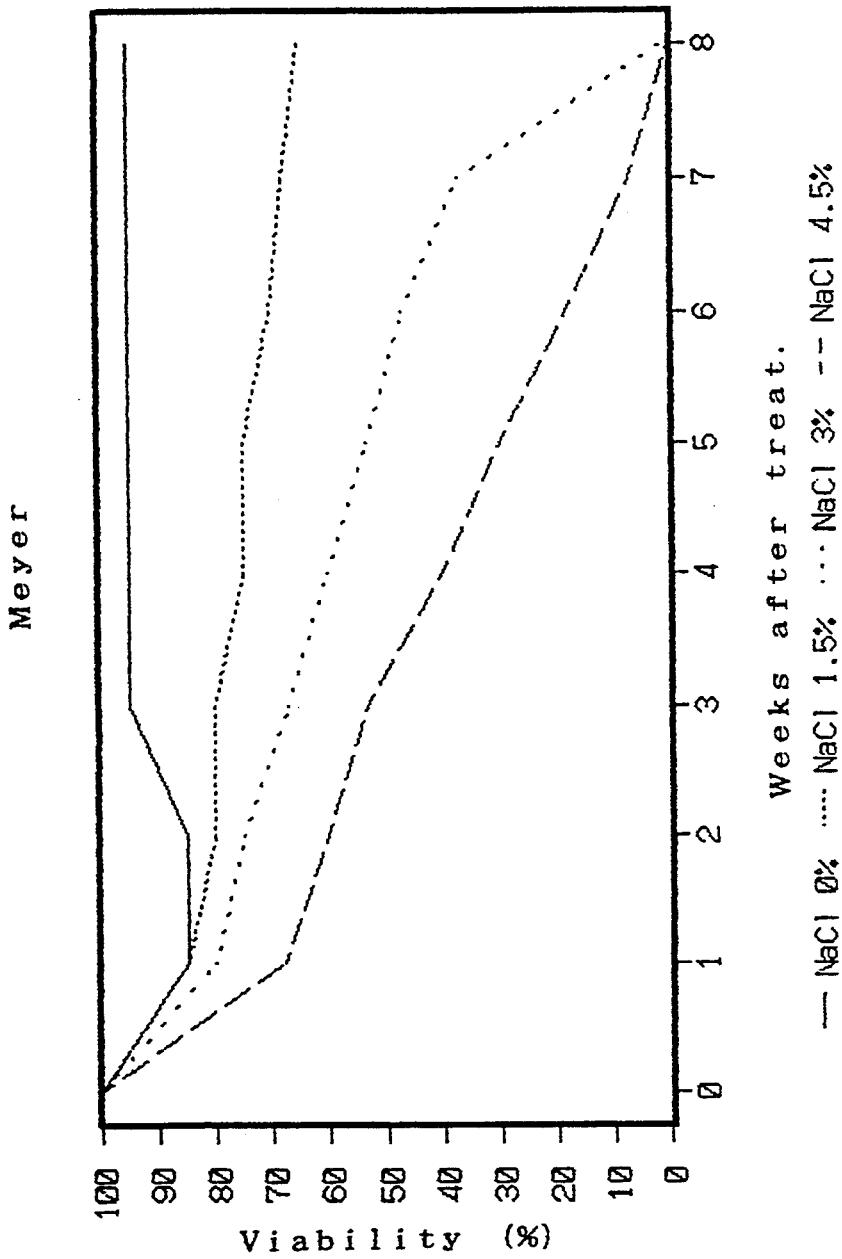

For each of the two strains, a plant with about 50 stems was planted in five Wagner pots (1/5000 a) and given once a week a sufficient amount of an aqueous NaCl solution at a predetermined concentration for examination of the salt resistance of the stem. The results, as shown in FIG. 10, indicate that the present variety GS90-18 exhibits higher viability and salt resistance than those of Meyer at every salt concentration. No difference could be observed in salt resistance between GS90-18 and the Tsukuba line.

As a result of the observation for drought resistance, there was no substantial resistance between GS9018 and Meyer. As compared with Meyer, GS90-18 has high treading resistance because of the formation of a dense sod of thinner leaves.

Like other Zoysia grasses, the present variety GS90-18 can grow readily without the application of fertilizer. However, in order to maintain and control the turf, variety GS90-18 can be fertilized as far as possible 3 to 10 times annually, depending on the desired rate of growth. Under conditions of soil and fertilization which promote a high growth rate, the frequency of trimming should be increased, but the frequency can be reduced by setting up suitable growth conditions where fertilization is restrained.

Once trimming in 2–3 weeks in enough for the present variety GS90-18 for use as turf in the home, as in the case with the original variety Tsukuba line and the variety Meyer. In winter, however, the present variety, unlike the original variety, and Myer is to be trimmed once in a month. Like the original variety, the present variety hardly presents thatch accumulation, as opposed to the variety Meyer presenting some accumulation of thatch.

The application of excess water or nitrogen fertilizers should be avoided, since these facilitate the occurrence of diseases and pests. The present variety GS90-18 has treading resistance, drought resistnace, salt resistance and shade tolerance.

Cultivation tests in 9 places in Japan indicate that the present variety is evergreen in the areas where the average lowest temperature in January and February is 2° C. or more and the lowest temperature is −4° C. or more.

Turf resulting from variety GS90-18 is not only useful in residential and park applications throughout the entire year, but is also suitable as a sport turf in a golf course or an athletic field, etc. In particular, damaged sport turf and a turf depot can be rapidly recovered because stolons of the present vareity can rapidly form a mat. The present strain forms a uniform and beautiful turf owing to vegetable propagation based on a signal genotype. The present strain keeps green stems and leaves even in winter and spring, so that unlike a turf becoming dormant, weed invasion can be significantly prevented and the cost for weeding can be reduced. Furthermore, variety GS90-18 provides a green carpet in all seasons for use in gardening, such as planting in city park or a factory site, and the attributes of nature can be created by the present variety when planted together with trees and the like. In general, less trimming, fertilizing, watering and other care procedures are required for Manila grass than are required for seed-grown turf and Bermuda grass, thus significantly reducing maintenance cost. The present variety GS90-18 is similar to other Manila grass, and can also be maintained with labor conserved.

We claim:

1. A variety of Manila grass plant, substantially as shown and described herein, characterized particularly by the ability to maintain green leaves for the entire year, and by somewhat straight grasses and slender leaf blades.

* * * * *

UNITED STATES PATENT AND TRADEMARK OFFICE

CERTIFICATE OF CORRECTION

PATENT NO. : PP 09089

DATED : 3/21/95

INVENTOR(S) : Takashi Yamagishi, Kenichi Nakagawa, Kouichi Mitsui, Shigeki Nagatomi, Kenzo Miyahara It is certified that error appears in the above-indentified patent and that said Letters Patent is hereby corrected as shown below:

On the title page, item [73]
Please add after

Assignee: Sumitomo Metal Industries, Ltd., Osaka, Japan

-- and National Institute of Agrobiological Resources, Ministry of Agriculture, Forestry & Fisheries, Ibaraki, Japan --

Signed and Sealed this

Second Day of July, 1996

*Attest:*

*Attesting Officer*

BRUCE LEHMAN

*Commissioner of Patents and Trademarks*